United States Patent [19]

Weigle et al.

[11] 4,415,493

[45] Nov. 15, 1983

[54] IMMUNE MODULATOR PEPTIDES

[75] Inventors: William O. Weigle, Del Mar; Edward L. Morgan, San Diego, both of Calif.

[73] Assignee: Scripps Clinic and Research Foundation, La Jolla, Calif.

[21] Appl. No.: 377,223

[22] Filed: May 11, 1982

[51] Int. Cl.³ .......................................... C07C 103/52
[52] U.S. Cl. .............................................. 260/112.5 R
[58] Field of Search ................................ 260/112.5 R

[56] References Cited

PUBLICATIONS

Biochemical and Biophysical Research Commun., vol. 71, No. 4, (1976), pp. 907–914.
Biochem. J., (1977), 165, 303–308.
Biochem. J., (1976), 155, 31–36.
The Journal of Immunology, 118, (1977), 388–394.
Morgan et al., J. Exp. Med. 150, 256–266, (1979).
Morgan et al., J. Exp. Med. 151, 1–11, (1980).
Morgan et al., J. Immunol. 124, 1330–1335, (1980).
Morgan et al., J. Supramolecular Structure 14, 201–208, (1980).
Morgan et al., J. Exp. Med. 152, 113–123, (1980).
Morgan et al., J. Immunol. 125, 1275–1279, (1980).
Michaelsen et al., J. Immunol. 119, 558–563, (1977).
Pardo et al., J. Immunol. 121, 1040–1044, (1978).
Connell et al., Can. J. Biochem. 57, 758–767, (1979).
Wang et al., J. Immunol. 125, 1048–1054, (1980).

*Primary Examiner*—Delbert R. Phillips
*Attorney, Agent, or Firm*—William C. Martens, Jr.; Arthur R. Whale

[57] ABSTRACT

A class of 23 or 24 amino acid peptides available by chemical synthesis or by enzymatic and chemical cleavage of IgG is described. The compounds are useful in modulating the immune response.

17 Claims, No Drawings

IMMUNE MODULATOR PEPTIDES

BACKGROUND OF THE INVENTION

This invention is directed to a class of polypeptides that are useful in modulating the immune response.

Immunoglobulins are proteins produced by plasma cells as one of the latter in a complex sequence of events initiated by antigen challenge of the host. The plasma cells, as another part of this sequence, are derived from B lymphocytes that have become activated by a mechanism or series of mechanisms that, to date, are not fully understood.

There are five classes of recognized immunoglobulins: IgG, IgA, IgM, IgD, and IgE. Of these, IgG represents the major portion of circulating immunoglobulins.

The immunoglobulin protein molecule is composed of four interconnected polypeptide chains, two of which are termed "light" chains and two "heavy" chains. Under this arrangement, the Ig molecule is divided into two identical portions, each of which comprises a light and a heavy chain linked by disulfide bridges formed from cysteine residues. The two resulting portions, in turn, are linked by disulfide bridges.

Each of the four chains is composed generally of two portions, a variable region ($V_L$ and $V_H$) extending from the amino-terminal and having highly variable amino acid sequences, and a constant region ($C_L$ and $C_H$) extending from the carboxy terminal and having generally constant amino acid sequences. Each of these regions represents a discrete portion of the Ig molecule. The $C_H$ region is further subdivided into three domains designated $C_H1$, $C_H2$, and $C_H3$ on the basis of constant homology regions.

It has been known for a number of years that the Ig molecule can be enzymatically cleaved into discrete fragments. The properties of these fragments then have been determined using a variety of biological assay systems.

Using papain, the IgG molecule can be cleaved, producing an "Fc" fragment and two "Fab" fragments. The Fc fragment represents the C-terminal portions of the two heavy chains joined by a disulfide bridge, and the Fab fragments are composed of the N-terminal portion of the heavy chain and the entire light chain joined by a disulfide bridge.

Pepsin and plasmin cleavages of the IgG molecule occur at sites closer to the heavy chain C-terminal and downstream of the disulfide bridge that joins the two heavy chains. The pepsin product, termed the "pFc'" fragment, and the plasmin product, thus represent C-terminal portions of the Fc fragment ($C_H3$ domain of IgG).

It has been recognized that certain biological activities reside in the Fc and pFc' fragments. Thus, mouse spleen B lymphocytes are induced to proliferate in the presence of papain-derived Fc fragments, [M. A. Berman and W. O. Weigle, J. Exp. Med. 146, 241 (1977)]. Furthermore, it has been observed that the proliferative response is dependent upon the presence of macrophages. It appears that macrophages enzymatically cleave the Fc fragment to a 14,000 MW subfragment, and the latter stimulates B cell proliferation [E. L. Morgan and W. O. Weigle, J. Exp. Med. 150, 256 (1979); and E. L. Morgan and W. O. Weigle, J Exp. Med. 151, 1 (1979)].

Subsequently, it was demonstrated that the Fc fragment has the ability in the presence of both macrophage and T cells to induce a polyclonal antibody response in mouse spleen cells [E. L. Morgan and W. O. Weigle, J. Immun. 124, 1330 (1980)].

Correspondingly, it was also demonstrated that the shorter fragment produced by plasmin digestion of IgG is active in producing a polyclonal antibody response [E. L. Morgan and W. O. Weigle, J. Supra-molecular Structure 14, 201 (1980)].

A class of small peptides now has been discovered. These peptides are useful in modulating the immune response and are available either synthetically using readily available peptide synthesis methods or by enzymatic and chemical cleavage of the IgG molecule. When produced by cleavage methodology, the IgG first is digested with plasmin after which the resulting segments are treated with cyanogen bromide. The resulting active fragment comprises 23 amino acids defined by residues 335–357 of the IgG molecule to which is attached, at the C-terminal, homoserine (Hse) resulting from the methionine (residue 358), the site of the CNBr cleavage. For an illustration of these structures, see, for example the sequence described in G. M. Edelman et al., Proc. Nat'l Acad. Sci. USA 63, 78 (1969).

As noted, the peptides of this invention are available synthetically. When so produced, the C-terminal homoserine may, if desired, be omitted.

It surprisingly has been discovered that relatively small peptides as defined by this invention exhibit a potentiation of the immune response in terms of their ability to activate T cells and natural killer cells, to initiate and/or promote B-cell differentiation leading to antibody production, and to regulate an existing immune response. These polypeptides are quite selective in their action in that, unlike the Fc fragment described above, these compounds do not induce a significant B cell proliferation.

It is to a class of such polypeptides that this invention is directed.

SUMMARY OF THE INVENTION

Therefore, this invention is directed to a class of compounds having the formula defined by a 23 amino acid sequence represented by residue 335–357 of an IgG molecule to which is bonded, by amide formation, at the carboxyl terminal, homoserine or the lactone produced by dehydration of homoserine.

Preferred compounds of this class are those having the formula H-Thr-Ile-Ser-Lys-Ala-Lys-Gly-Gln-Pro-Arg-Glu-Pro-Gln-Val-Tyr-Thr-Leu-Pro-Pro-Ser-Arg-Glu-Glu-Hse in which Hse is homoserine or homoserine lactone.

This invention is also directed to a class of compounds having the formula

R-Thr-a-b-Lys-d-e-f-g-h-j-k-l-m-n-p-q-t-u-Pro-v-w-x-y-(z)$_n$-R$_1$ in which each amino acid residue has an L-configuration; R is hydrogen or $C_1$-$C_3$ alkyl; R$_1$ is OH or NR$_3$R$_4$ in which R$_3$ and R$_4$ independently are hydrogen or $C_1$-$C_3$ alkyl;

a is Ile or Leu;
b is Ser or Ala;
d is Ala, Thr, Pro, Val, or Ser;
e is Lys, Arg, Thr, or Gly;
f is Gly, Val, or Asn;
g is Gln, Lys, Ser, Glu, Pro, Ala, Asn, or Thr;
h is Pro, Val, Thr, or Phe;
j is Arg, Leu, Pro, or Phe;
k is Glu, Ala, Ile, Met, or Pro;

l is Pro, Lys, or Gln;
m is Gln, Glu, or Val;
n is Val or His;
p is Tyr, His, or Leu;
q is Thr, Val, or Leu;
t is Leu, Ile, Met, or Pro;
u is Pro or Gly;
v is Ser or Pro;
w is Arg, Gln, Glu, or Ser;
x is Glu, Asp, Gln, or Asn;
y is Glu, Gln, Gly, or Leu;
z is Hse; and r is 0 or 1.

A preferred subclass is represented by those compounds in which
a is Ile;
b is Ser;
d is Ala, Thr, Pro, or Ser;
e is Lys or Arg;
f is Gly;
g is Gln, Lys, Ser, or Pro;
h is Pro or Val;
j is Arg or Leu;
k is Glu, Ala, Ile, or Met;
l is Pro;
m is Gln or Glu;
n is Val;
p is Tyr;
q is Thr, Val, or Leu;
t is Leu, Ile, or Met;
u is Pro or Gly;
v is Ser or Pro;
w is Arg;
x is Glu or Asp; and
y is Glu or Gln.

A more preferred subclass is represented by those compounds in which
a is Ile;
b is Ser;
d is Ala, Thr, or Ser;
e is Lys or Arg;
f is Gly;
g is Gln;
h is Pro;
j is Arg;
k is Glu;
l is Pro;
m is Gln;
n is Val;
p is Tyr;
q is Thr;
t is Leu;
u is Pro or Gly;
v is Ser or Pro;
w is Arg;
x is Glu or Asp; and
y is Glu or Gln.

A further more preferred subclass is represented by those compounds in which
a is Ile;
b is Ser;
d is Ala or Thr;
e is Lys;
f is Gly;
g is Gln;
h is Pro;
j is Arg;
k is Glu;
l is Pro;
m is Glu or Gln;
n is Val;
p is Tyr;
q is Thr;
t is Leu;
u is Pro;
v is Ser;
w is Arg or Gln;
x is Glu, Asp, or Gln; and
y is Glu or Gly.

Examples of preferred amino acid sequences are:
R-Thr-Ile-Ser-Lys-Ala-Lys-Gly-Gln-Pro-Arg-Glu-Pro-Gln-Val-Tyr-Thr-Leu-Pro-Pro-Ser-Arg-Glu-Glu-$R_1$;

R-Thr-Ile-Ser-Lys-Ala-Lys-Gly-Gln-Pro-Arg-Glu-Pro-Gln-Val-Tyr-Thr-Leu-Pro-Pro-Ser-Arg-Asp-Glu-$R_1$;

R-Thr-Ile-Ser-Lys-Thr-Lys-Gly-Gln-Pro-Arg-Glu-Pro-Gln-Val-Tyr-Thr-Leu-Pro-Pro-Ser-Arg-Glu-Glu-$R_1$;

R-Thr-Ile-Ser-Lys-Thr-Lys-Gly-Gln-Pro-Arg-Glu-Pro-Glu-Val-Tyr-Thr-Leu-Pro-Pro-Ser-Arg-Glu-Glu-$R_1$;

R-Thr-Ile-Ser-Lys-Ala-Lys-Gly-Gln-Pro-Arg-Glu-Pro-Gln-Val-Tyr-Thr-Leu-Pro-Pro-Ser-Gln-Glu-Glu-$R_1$;

R-Thr-Ile-Ser-Lys-Ala-Lys-Gly-Pro-Pro-Arg-Ile-Pro-m-Val-Tyr-Leu-Leu-Pro-Pro-Pro-Arg-x-y-$R_1$;

R-Thr-Ile-Ser-Lys-Thr-Lys-Gly-Gln-Pro-Arg-Glu-Pro-Gln-Val-Tyr-Thr-Leu-Pro-Pro-Ser-Arg-x-Gly-$R_1$;

R-Thr-Ile-Ala-Lys-Val-Thr-Val-Asn-Thr-Phe-Pro-Pro-Gln-Val-His-Leu-Leu-Pro-Pro-Pro-Ser-Glu-Glu-$R_1$; and R-Thr-Leu-Ser-Lys-Ser-Gly-Asn-Thr-Phe-Arg-Pro-Gln-Val-His-Leu-Leu-Pro-Pro-Pro-Ser-w-x-Leu-$R_1$.

DETAILED DESCRIPTION OF THE INVENTION

As noted, this invention is directed to a class of polypeptides useful in modulating an immune response.

The compounds of this invention can be prepared by enzymatic and chemical cleavage of IgG. The IgG, obtained by routine methodology, can be purified by ammonium sulfate fractionation followed by DEAE cellulose chromatography using 0.01 M phosphate buffer, pH8, as eluant.

The recovered IgG then is digested with plasmin generally for 20–30 hours at an elevated temperature of about 37° C. The active fragment of the resulting digested IgG can be separated on Sephadex G-100 using 0.01 M phosphate buffer, pH7, as eluant.

The active portion then is treated with CNBr according to recognized procedures. These generally involve dissolving the product recovered from plasmin digestion in 70–90% formic acid containing an excess of CNBr. Cleavage is allowed to proceed at room temperature over an extended period (about 24 hours). The desired peptide product, a sequence comprising residues 335–358 of the IgG, molecule, in which residue 358 (methionine) is changed to homoserine or homoserine lactone by reason of the CNBr cleavage reaction, can be recovered by routine chromatographic separation, including molecular exclusion high performance liquid chromatography (HPCL) and reverse phase HPLC. The resulting sequence, comprising residues 335–358 as modified by CNBr cleavage, represents compounds of this invention.

The compounds of this invention also can be prepared by any of a variety of recognized peptide synthesis techniques including classical (solution) methods, solid phase methods, and the more recently available recombinant DNA methods.

A preferred method of preparation of the compounds of this invention is by the solid phase technique in which the amino acid sequence is constructed sequentially from an initial, insoluble, resin-supported C-terminal amino acid. Techniques for the solid phase method are described by J. Stewart et al., *Solid Phase Peptide Synthesis*, Freeman and Co., San Francisco, 1969.

In general, in the solid phase method, the amino acid corresponding to the C-terminal amino acid residue of the desired peptide is anchored to an insoluble resin support, and the peptide chain then is formed beginning at the resin-supported C-terminal amino acid. Individual amino acids are introduced sequentially until the desired amino acid sequence is obtained. Alternatively, small peptide fragments can be prepared and introduced into the peptide chain in the desired order. The peptide chain remains attached to the resin throughout synthesis, and, upon completion of the chain, the peptide is cleaved from the resin.

The peptide chain is attached to the polystyrene resin by means of an ester linkage formed between the carboxyl group of the C-terminal moiety and one of the methylene groups present on the resin matrix as sites for such attachment. The polystyrene resin is a styrene polymer which is cross-linked by the addition of about 0.5 to about 3% divinylbenzene and which is chloromethylated or hydroxymethylated to provide sites for ester formation. An example of a hydroxymethylated resin is described by Bodanszky et al., Chem. Ind. (London), 38, 1597-98 (1966). A chloromethylated polystyrene resin is commercially available from Lab System, Inc., San Mateo, California. The resin is also described by Stewart et al., *Solid Phase Peptide Synthesis*, Freeman and Co., San Francisco, California, pp. 1–6.

The amino acids are coupled using techniques well-known in the art for the formation of peptide bonds. One method involves converting the amino acid to a derivative that will render the carboxyl group more susceptible to reaction with the free N-terminal amino group of the peptide fragment. For example, the amino acid can be converted to a mixed anhydride by reaction of a protected amino acid with ethyl chloroformate, phenyl chloroformate, sec-butyl chloroformate, isobutyl chloroformate, pivaloyl chloride, or like acid chlorides. Alternatively, the amino acid can be converted to an active ester such as a 2,4,5-trichlorophenyl ester, a pentachlorophenyl ester, a p-nitrophenyl ester, an ester formed from N-hydroxysuccinimide, or an ester formed from 1-hydroxybenzotriazole.

Another coupling method involves use of a suitable coupling agent, such as N,N'-dicyclohexylcarbodiimide (DCC) or N,N'-diisopropylcarbodiimide (DIC). Other appropriate coupling agents will be apparent to those skilled in the art. [See Schroder and Lubke, *The Peptides*, Academic Press, 1965, Chapter III.]

It should be recognized that the α-amino group of each amino acid employed in the peptide synthesis must be protected during the coupling reaction to prevent side reactions involving the reactive α-amino function. It should also be recognized that certain amino acids contain reactive side-chain functional groups (e.g. sulfhydryl, ε-amino, carboxyl, and hydroxyl), and that such functional groups must also be protected both during the initial and subsequent coupling steps. Suitable protecting groups are known in the art [See for example, *Protective Groups In Organic Chemistry*, M. McOmie, Editor, Plenum Press, N.Y., 1973.]

In selecting a particular protecting group, certain conditions must be observed. An α-amino protecting group (1) must be stable, (2) must render the α-amino function inert under the conditions employed in the coupling reaction, and (3) must be readily removable after the coupling reaction under conditions that will not remove side chain protecting groups and will not alter the structure of the peptide fragment. A side chain protecting group (1) must render the side chain functional group inert under the conditions employed in the coupling reaction, (2) must be stable under the conditions employed in removing the α-amino protecting group, and (3) must be readily removable upon completion of the desired amino acid sequence under reaction conditions that will not alter the structure of the peptide chain.

It will be apparent to those skilled in the art that the protecting groups known to be useful for peptide synthesis will vary in reactivity the agents employed for their removal. For example, certain protecting groups, such as triphenylmethyl and 2-(p-biphenylyl)isopropyloxycarbonyl are very labile and can be cleaved under mild acid conditions. Other protecting groups, such as t-butyloxycarbonyl, t-amyloxycarbonyl, adamantyloxycarbonyl, and p-methoxybenzyloxycarbonyl, are less liable and require moderately strong acids, such as trifluoroacetic, hydrochloric, or boron trifluoride in acetic acid, for their removal. Still other protecting groups, such as benzyloxycarbonyl, halobenzyloxycarbonyl, p-nitrobenzyloxycarbonyl, cycloalkyloxycarbonyl, and isopropyloxycarbonyl, are even less labile and require strong acids, such as hydrogen fluoride, hydrogen bromide, or boron trifluoroacetate in trifluoroacetic acid, for their removal.

Illustrative examples of amino acid protecting groups are set forth below.

A. For an α-amino group, protection may include (a) acyl-type groups, such as formyl, trifluoracetyl, phthalyl, p-toluenesulfonyl (tosyl), benzenesulfonyl, nitrophenylsulfenyl, and the like; (b) aromatic urethane-type groups, such as benzyloxycarbonyl and substituted benzyloxycarbonyl, such as, for example, p-chlorobenzyloxycarbonyl, p-bromobenzyloxycarbonyl, p-nitrobenzyloxycarbonyl, and p-methoxybenzyloxycarbonyl, o-chlorobenzyloxycarbonyl, 2,4-dichlorobenzyloxycarbonyl, 2,6-dichlorobenzyloxycarbonyl, and the like; (c) aliphatic urethane-type groups such as t-butyloxycarbonyl, t-amyloxycarbonyl, isopropyloxycarbonyl, 2-(p-biphenylyl)-isopropyloxycarbonyl, allyloxycarbonyl, and the like; (d) cycloalkyl urethane-type groups such as cyclopentyloxycarbonyl, cyclohexyloxycarbonyl, cycloheptyloxycarbonyl, adamantyloxycarbonyl, and the like; (e) thiourethane-type groups such as phenylthiocarbonyl; (f) alkyl-type groups such as triphenylmethyl, and (g) trialkylsilane groups, such as trimethylsilane. A preferred α-amino protecting group is t-butyloxycarbonyl (BOC).

B. For the ε-amino protecting group present in lysine, protection may be by any of the groups mentioned hereinabove for protection of an α-amino group.

Typical groups include, for example, benzyloxycarbonyl, p-chlorobenzyloxycarbonyl, p-bromobenzyloxycarbonyl, o-chlorobenzyloxycarbonyl, 2,6-dichlorobenzyloxycarbonyl, 2,4-dichlorobenzyloxycarbonyl, o-bromobenzyloxycarbonyl, p-nitrobenzyloxycarbonyl t-butyloxycarbonyl, isopropyloxycarbonyl, t-amyloxycarbonyl, cyclopentyloxycarbonyl, cyclohexyloxycarbonyl, cycloheptyloxycarbonyl, adamantyloxycarbonyl, p-toluenesulfonyl, and the like. The preferred ε-amino protecting group is o-chlorobenzyloxycarbonyl (ClBzl).

C. For the hydroxyl group of serine, threonine, or tyrosine, protection may be, for example, by $C_1$–$C_4$ alkyl, such as methyl, ethyl, and t-butyl; benzyl; substituted benzyl, such as p-methoxybenzyl, p-nitrobenzyl, p-chlorobenzyl, and o-chlorobenzyl; $C_1$–$C_3$ alkanoyl, such as formyl, acetyl, and propionyl; triphenylmethyl; or benzoyl. The preferred hydroxyl protecting group is benzyl (Bzl).

D. For the carboxyl group of aspartic acid or glutamic acid, protection may be, for example, by esterification using groups such as benzyl, t-butyl, cyclohexyl, cyclopentyl, and the like. The current groups of choice are cyclohexyl and cyclopentyl.

Upon completion of the desired peptide sequence, the protected peptide must be cleaved from the resin support, and all protecting groups must be removed. The cleavage reaction and removal of the protecting groups may be accomplished simultaneously or stepwise. When the resin support is a chloromethylated polystyrene resin, the bond anchoring the peptide to the resin is an ester linkage formed between the free carboxyl group of the C-terminal moiety and one of the many chloromethyl groups present on the resin matrix. It will be recognized that the anchoring bond can be cleaved by reagents which are known to be capable of breaking an ester linkage and of penetrating the resin matrix. One especially convenient method is by treatment with liquid hydrogen fluoride. This reagent not only will cleave the peptide from the resin but will also remove all protecting groups. Hence, use of this reagent will directly afford the fully deprotected peptide. When it is desired to cleave the peptide without removing protecting groups, the protected peptide-resin can undergo methanolysis to give the protected peptide in which the C-terminal carboxyl group is methylated. The methyl ester can then be hydrolyzed under mild, alkaline conditions to give the free C-terminal carboxyl. The protecting groups on the peptide chain then can be removed by treatment with a strong acid, such as liquid hydrogen fluoride. A particularly useful technique for methanolysis is that of G. Moore et al., Peptides, Proc. 5th Amer. Pept. Symp., M. Goodman and J. Meinhofer, Eds., John Wiley, N.Y., 1977, pp. 518–521, in which the protected peptide-resin is treated with methanol and potassium cyanide in the presence of crown ether.

Another method for cleaving the protected peptide from the resin is by ammonolysis or by treatment with hydrazine. The resulting C-terminal amide or hydrazide can be hydrolyzed to the free C-terminal carboxyl, and the protecting groups can be removed conventionally.

It will also be recognized that the protecting group present on the N-terminal α-amino group may be removed preferentially either before or after the protected peptide is cleaved from the resin support.

For the sake of convenience and understanding, the amino acids referred herein are described both by their improved shorthand three-letter and single-letter designations.

These designations are as follows:

|  | 3-letter | 1-letter |
|---|---|---|
| Alanine | Ala | A |
| Arginine | Arg | R |
| Asparagine | Asn | N |
| Aspartic Acid | Asp | D |
| Glutamic Acid | Glu | E |
| Glutamine | Gln | Q |
| Glycine | Gly | G |
| Histidine | His | H |
| Homoserine | Hse | — |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tyrosine | Tyr | Y |
| Valine | Val | V |

Using the convenient single-letter amino acid designation, the following peptides are illustrative of the compounds of this invention. Although not designated in the compounds illustrated below, it will be recognized that any of the depicted compounds may comprise any of the following:

(1) an alkyl group at its amino terminal nitrogen;
(2) an alkyl substituted or unsubstituted amide at its carboxyl terminal; and
(3) an added homoserine at its carboxyl terminal, which homoserine may be derivatized by dehydration to its corresponding lactone.

T-I-S-K-A-K-G-Q-P-R-E-P-Q-V-Y-T-L-P-P-S-R-E-E;

T-I-S-K-A-K-G-Q-P-R-E-P-Q-V-Y-T-L-P-P-S-R-D-E;

T-I-S-K-T-K-G-Q-P-R-E-P-Q-V-Y-T-L-P-P-S-R-E-E;

T-I-S-K-T-K-G-Q-P-R-E-P-E-V-Y-T-L-P-P-S-R-E-E;

T-I-S-K-A-K-G-Q-P-R-E-P-Q-V-Y-T-L-P-P-S-Q-E-E;

T-I-S-K-A-K-G-P-P-R-I-P-Q-V-Y-L-L-P-P-P-R-D-E;

T-I-S-K-T-K-G-Q-P-R-E-P-Q-V-Y-T-L-P-P-S-R-E-G;

T-I-A-K-V-T-V-N-T-F-P-P-Q-V-H-L-L-P-P-P-S-E-E;

T-L-S-K-S-G-N-T-F-R-P-Q-V-H-L-L-P-P-P-S-Q-E-L;

T-I-S-K-S-R-G-Q-P-R-E-P-Q-V-Y-T-L-G-P-S-R-D-Q;

T-L-A-K-V-G-V-S-F-L-M-P-E-H-Y-L-I-P-P-P-S-D-L;

T-I-A-K-P-G-V-K-P-R-E-K-E-V-Y-T-L-P-P-S-R-E-E;

T-I-S-K-T-R-G-Q-P-R-E-P-Q-V-Y-T-L-P-P-S-S-N-L;

T-L-S-K-V-K-G-Q-P-R-E-P-Q-V-Y-T-M-P-P-S-R-E-E;

T-I-S-K-P-G-G-Q-P-R-P-P-E-V-Y-T-L-P-P-S-R-E-E;

T-I-S-K-S-T-G-T-P-R-I-P-V-V-Y-T-L-P-P-S-Q-E-E;

T-I-S-K-A-K-V-S-P-R-A-P-Q-V-H-L-L-P-P-P-R-D-E;

T-I-S-K-T-T-G-Q-P-R-A-P-V-V-Y-T-L-P-P-S-R-E-G;

T-I-A-K-V-T-V-T-T-F-P-P-Q-V-H-L-L-G-P-P-S-E-E;

T-L-A-K-T-G-N-T-F-R-P-Q-V-H-H-L-P-P-P-S-Q-E-L;

T-I-S-K-P-R-V-Q-F-R-M-P-V-V-Y-T-L-G-P-S-R-D-Q;

T-L-A-K-V-G-V-S-F-L-E-P-E-H-Y-L-I-P-P-P-R-E-E; and the like.

The compounds of this invention, in view of their effect in modulating immune response, have wide applicability. They can be used, for example, in treating cancer, parasitic infections, and a wide range of autoimmune diseases.

The compounds of this invention can be used in a variety of pharmaceutical compositions and formulations and can be administered by a variety of conventional routes, such as intramuscular, intravenous, subcutaneous, intraperitoneal, and oral.

In administering the compounds of this invention parenterally or intraperitoneally, the pharmaceutical forms suitable for injection include sterile aqueous solutions or dispersions and sterile powders for reconstitution into sterile injectible solutions or dispersions. The carrier can be a solvent or dispersing medium containing, for example, water, ethanol, polyol (for example glycerol, propylene glycol, liquid polyethylene glycol, and the like), suitable mixtures thereof, and vegetable oils. Proper fluidity can be maintained, for example, by the use of a coating such as lecithin, by the maintenance of the required particle size in the case of dispersion and by the use of surfactants. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin.

Sterile injectable solutions can be prepared by incorporating the compounds of this invention in the required amount of the appropriate solvent with various of the other ingredients, as desired.

If desired, and for more effective distribution, the compounds can be incorporated into slow release or targeted delivery systems such as polymer matrices, liposomes, and microspheres.

As noted, the compounds of this invention can also be administered orally. They can be used with an inert diluent or a pharmaceutical carrier which can take the form of capsules, tablets, suspensions, emulsions, solutions, dispersible powders, and the like. Moreover, the compounds of this invention can be administered either alone or as a mixture of a plurality of active ingredients.

Doses of the compounds of this invention are administered to the recipient for a period during which modulation of the immune response is desired. The weight of the recipient and mode of administration will have an influence upon the size of the dose necessary to induce a particular response. Generally, for parenteral or intraperitoneal administration, the dose will be from about 200 μg. to about 10 mg. per kilogram (kg.) body weight of the recipient per day throughout the period of desired immune response modulation. Preferably, the compound is administered in an amount from about 500 μg. to about 5 mg. per kg. body weight daily.

It is especially advantageous to formulate the compounds of this invention in unit dosage form for ease of administration and uniformity of dosage. Unit dosage form as used herein refers to a physically discrete unit suited as unitary dosages for the subject to be treated. Each unit contains a predetermined quantity of the compound calculated to produce the desired therapeutic effect in association with the pharmaceutically acceptable carrier. The specific unit dosage form is dictated by and directly dependent upon (a) the unique characteristics of the particular composition and (b) the particular therapeutic effect to be achieved.

The following examples are illustrative of this invention. They are not intended to be limiting upon the scope thereof.

EXAMPLE 1

Preparation of L-Threonyl-L-isoleucyl-L-seryl-L-lysyl-L-alanyl-L-lysyl-glycyl-L-glutaminyl-L-prolpl-L-arginyl-L-glutamyl-L-prolyl-L-glutaminyl-L-valyl-L-tyrosyl-L-threonyl-L-leucyl-L-prolyl-L-prolyl-L-seryl-L-arginyl-L-glutamyl-L-glutamyl-L-homoserine lactone from IgG, and Its Biological Potency.

$IgG_1$ (Pet), 100 mg., obtained from Dr. Hans L. Spiegelberg, Scripps Clinic and Research Foundation, was inoculated with 1.2 mg. of plasmin for 24 hours at 37° C. and pH 7.2. The resulting digested $IgG_1$ then was separated on a Sephadex G-100 column (1.5 cm.×75 cm.) using 0.01 M phosphate buffer, pH7, as eluant.

Two peaks were seen. Each was collected and analyzed for its ability to induce murine splenic B cells to secrete polyclonal antibody. The method is described in E. L. Morgan and W. O. Weigle, J. Immun. 124, 1330 (1980). As the following shows, only Peak II contains biologically active material.

| | $PFC/10^6$ |
|---|---|
| Peak I | 10 ± 3 |
| Peak II | 98 ± 1 |

The material obtained from Peak II (50 mg.) was dissolved in 0.7 ml. of 88% formic acid. A 100-fold excess (w/w) of CNBr was added, and the mixture was allowed to react overnight at room temperature. The resulting mixture was frozen on dry ice and lyophilized to remove excess CNBr.

The product from lyophilization was subjected to molecular exclusion high performance liquid chromatography (HPLC) using two protein I-60 columns (7.8 mm.×30 cm) (Waters Associates, Inc., Medford, Mass.) in tandem, in line with a Waters HPLC apparatus. The mobile phase buffer consisted of 0.1 M $NH_4HCO_3$. Elution was carried out at a flow rate of 1 ml./minute and was monitored at 210 nm. Two peaks, designated Pools 1 and 2, were recovered and were assayed for ability to induce a polyclonal antibody response. The following results were obtained:

| | $PFC/10^6$ |
|---|---|
| Pool 1 | 11 ± 1 |
| Pool 2 | 151 ± 15 |

From the above, it is evident that the active fragment is in Pool 2.

The material from Pool 2 was subjected to reverse phase HPLC using a TMS-Zorbax (Dupont Instrument, Wilmington, Del.) column (4.6 mm.×25 cm.). Peptide elution was achieved using a linear gradient of 0–100% buffer "B" in buffer "A" developed 45 minutes at a flow rate of 1 ml./min. Buffer "A" was composed of 5% $CH_3CN$ in 0.1% $H_3PO_4$ and buffer "B" of 95% $CH_3CN$ in 0.1% $H_3PO_4$. The elution was monitored by absorbance at 210 nm.

Five pools (A-E) were collected, and each was assessed for its ability to induce murine splenic B cells to secrete polyclonal antibody. Following are the results which were obtained:

|        | $PFC/10^6$ |
|--------|------------|
| Pool A | 95 ± 2     |
| Pool B | 19 ± 6     |
| Pool C | 10 ± 4     |
| Pool D | 3 ± 3      |
| Pool E | 2 ± 1      |

The above results reveal that only the material from Pool A had the capacity to induce polyclonal antibody production.

The amino acid composition of the peptide of Pool A was determined, using a Beckman Model 121M amino acid analyzer. The sample was hydrolyzed for 24 hours in an evacuated ampoule 0.5 ml. 1 N HCl, 1 ml. 88% phenol, and 1 ml. 2-mercaptoethanol. The following results, on a mole/mole basis, were obtained:

Thr, 2.02; Ser, 1.98; Glu, 5.01; Pro, 4.41; Gly, 1.08; Ala, 1.01; Val, 0.97; Ile, 0.98; Leu, 1.07; Tyr, 0.57; Lys, 1.97; Arg, 2.04; His, 0.11; Asp, 0.0; Phe, 0.0; Met 0.0*
*Methionine was converted to homoserine lactone by CNBr cleavage and therefore was not quantitated.

EXAMPLE 2

Preparation of
L-Threonyl-L-isoleucyl-L-seryl-L-lysyl-L-alanyl-L-lysyl-L-glycyl-L-glutaminyl-L-prolyl-L-arginyl-L-glutamyl-L-prolyl-L-glutaminyl-L-valyl-L-tyrosyl-L-threonyl-L-leucyl-L-prolyl-L-prolyl-L-seryl-L-arginyl-L-glutamyl-L-glutamic acid.

A. N-t-Butyloxycarbonyl-L-(γ-cyclopentyl)glutamic acid hydroxymethyl-polystyrene resin ester To 50 ml. of 95% ethanol were added 3.784 g. (12.0 mmol.) of N-t-butyloxycarbonyl-L-(γ-cyclopentyl)-glutamic acid. To the resulting solution then were added 12.0 ml. of 1 N cesium bicarbonate solution with accompanying $CO_2$ evolution. The mixture was evaporated in vacuo to an oil. The oil was dissolved in a mixture of benzene and 95% ethanol, and the resulting solution was evaporated again. This water-azeotroping procedure was repeated until the water had been removed with formation of a white solid.

The cesium salt of the protected glutamic acid was dissolved in 200 ml. of N,N-dimethylformamide (DMF), and the mixture was placed in a vessel equipped with a stirrer and a drying tube and in the presence of a dry $N_2$ atmosphere. With maintenance of the $N_2$ atmosphere, 20.0 g. of chloromethylated polystyrene resin (Merrifield resin) (about 0.7 mmol. chlorine per gram resin) were added. The mixture was stirred at 50° C. for about 72 hours.

The resin was collected by filtration, washed three times with a sequence of 85% DMF:15% $H_2O$ followed by DMF, three times with 95% ethanol, and once with DMF. The resin then was dried in vacu to obtain about 21 grams which, by analysis, showed about 0.2 mmol. Glu/g. resin.

The resin was suspended in 200 ml. of DMF, and 5.96 g. (31 mmol.) of cesium acetate (hydrate) were added. The mixture was stirred in a dry $N_2$ atmosphere at 60° C. for about 72 hours.

The resin was collected by filtration and washed with DMF, 85% DMF, and 95% ethanol using a sequence similar to that previously described. The fines were removed by suspending the resin in $CHCl_3$ (6 portions) in a separatory funnel and drawing off the $CHCl_3$. The resin was filtered, washed with 95% ethanol, and dried overnight in vacuo at 45° C.

B.
N-t-Butyloxycarbonyl-L-(O-benzyl)threonyl-L-isoleucyl-L-(O-benzyl)seryl-L-(N$^\epsilon$-o-chlorobenzyloxycarbonyl)lysyl-L-alanyl-L-(N$^\epsilon$-o-chlorobenzyloxycarbonyl)lysyl-glycyl-L-glutaminyl-L-prolyl-L-(N-p-tosyl)arginyl-L-(γ-cyclopentyl)glutamyl-L-prolyl-L-glutaminyl-L-valyl-L-[O-(2,6-dichlorobenzyl)]-tyrosyl-L-(O-benzyl)threonyl-L-leucyl-L-prolyl-L-prolyl-L-(O-benzyl)seryl-L-(N-p-tosyl)arginyl-L-(γ-cyclopentyl)glutamyl-L-(γ-cyclopentyl)-glutamic acid hydroxymethyl-polystyrene resin ester N-t-Butyloxycarbonyl-L-(γ-cyclopentyl)-glutamic acid hydroxymethyl-polystyrene resin ester (20.15 g.), as prepared in Part A, was placed into a Beckman 990B peptide synthesizer and treated with the following sequence of protected amino acids using one or more of the schedules set forth below.

1. N-t-butyloxycarbonyl-L-(γ-cyclopentyl)-glutamic acid
   Schedule A—5.05 g.
   Schedule B—3.78 g.
2. N-t-butyloxycarbonyl-L-(N-p-tosyl)arginine
   Schedule A—6.85 g.$^a$
   Schedule B—5.14 g.
   Schedule B—5.14 g.$^b$
3. N-t-butyloxycarbonyl-L-(O-benzyl)serine
   Schedule A—4.72 g.
   Schedule B—4.72 g.
4. N-t-butyloxycarbonyl-L-proline
   Schedule A—3.46 g.
   Schedule B—3.46 g.
5. N-t-butyloxycarbonyl-L-leucyl-L-proline
   Schedule A—5.27 g.
   Schedule B—5.27 g.
6. N-t-butyloxycarbonyl-L-(O-benzyl)threonine
   Schedule A—4.95 g.
   Schedule B—4.95 g.
7. N-t-butyloxycarbonyl-L-[O-(2,6-dichlorobenzyl)-]tyrosine
   Schedule A—7.04 g.
   Schedule B—7.04 g.
8. N-t-butyloxycarbonyl-L-valine
   Schedule A—3.48 g.
   Schedule B—2.60 g.
   Schedule B—2.60 g.$^b$
9. N-t-butyloxycarbonyl-L-glutamine, p-nitrophenyl ester
   Schedule C—5.88 g.
   Schedule D—5.88 g.
10. N-t-butyloxycarbonyl-L-proline
    Schedule A—3.46 g.
    Schedule B—3.46 g.

11. N-t-butyloxycarbonyl-L-(γ-cyclopentyl)-glutamic acid
 Schedule A—5.05 g.
 Schedule B—3.78 g.
12. N-t-butyloxycarbonyl-L-(N-p-tosyl)-arginine
 Schedule A—6.85 g.[a]
 Schedule B—5.14 g.
 Schedule B—5.14 g.[b]
13. N-t-butyloxycarbonyl-L-proline
 Schedule A—3.46 g.
 Schedule B—3.46 g.
14. N-t-butyloxycarbonyl-L-glutamine, p-nitrophenyl ester
 Schedule C—5.88 g.
 Schedule D—5.88 g.
15. N-t-butyloxycarbonyl-glycine
 Schedule A—2.80 g.
16. N-t-butyloxycarbonyl-L-(N$^\epsilon$-o-chlorobenzyloxycarbonyl)lysine
 Schedule A—6.64 g.
 Schedule B—6.64 g.
17. N-t-butyloxycarbonyl-L-alanine
 Schedule A—3.03 g.
18. N-t-butyloxycarbonyl-L-(N$^\epsilon$-o-chlorobenzyloxycarbonyl)lysine
 Schedule A—6.64 g.
 Schedule B—6.64 g.
19. N-t-butyloxycarbonyl-L-(O-benzyl)serine
 Schedule A—4.72 g.
 Schedule B—4.72 g.
20. N-t-butyloxycarbonyl-L-isoleucine
 Schedule A—3.70 g.
 Schedule B—3.70 g.
21. N-t-butyloxycarbonyl-L-(O-benzyl)threonine
 Schedule A—4.95 g.
 Schedule B—4.95 g.

Footnotes:
 (a) 1:9 DMF:CH$_2$Cl$_2$
 (b) DMF

SCHEDULE A

1. Wash three times for three minutes each with 6.5 ml. of CH$_2$Cl$_2$ per gram resin.
2. To remove the t-butyloxycarbonyl α-amino protecting group, treat twice for twenty minutes each with 8.4 ml. per gram resin of a mixture of trifluoroacetic acid (29%), CH$_2$Cl$_2$ (65%), and triethylsilane (6%).
3. Wash three times for three minutes each with 6.5 ml. of CH$_2$Cl$_2$ per gram resin.
4. Wash three times for three minutes each with 6.5 ml. per gram resin of a mixture of 90% t-BuOH and 10% t-AmOH.
5. Wash three times for three minutes each with 6.5 ml. of CH$_2$Cl$_2$ per gram resin.
6. For neutralization, treat three times for three minutes each with 6.5 ml. per gram resin of a mixture of 4% diisopropylethylamine in CH$_2$Cl$_2$.
7. Wash three times for three minutes each with 6.5 ml. of CH$_2$Cl$_2$ per gram resin.
8. Wash three times for three minutes each with 6.5 ml. per gram resin of a mixture of 90% t-BuOH and 10% t-AmOH.
9. Wash three times for three minutes each with 6.5 ml. of CH$_2$Cl$_2$ per gram resin.
10. To couple the amino acid, treat with the protected amino acid and N,N'-dicyclohexylcarbodiimide (50% on molar basis relative to the amino acid) in 80 ml. of CH$_2$Cl$_2$ for 110 minutes.
11. Wash three times for three minutes each with 6.5 ml. of CH$_2$Cl$_2$ per gram resin.
12. Wash three times for three minutes each with 6.5 ml. per gram resin of a mixture of 90% t-BuOH and 10% t-AmOH.
13. Wash three times for three minutes each with 6.5 ml. of CH$_2$Cl$_2$ per gram resin.
14. For neutralization, treat three times for three minutes each with 6.5 ml. per gram resin of a mixture of 4% diisopropylethylamine in CH$_2$Cl$_2$.
15. Wash three times for three minutes each with 6.5 ml. of CH$_2$Cl$_2$ per gram resin.
16. Wash three times for three minutes each with 6.5 ml. per gram resin of a mixture of 90% t-BuOH and 10% t-AmOH.
17. Wash three times for three minutes each with 6.5 ml. of CH$_2$Cl$_2$ per gram resin.

SCHEDULE B

1. Wash three times for three minutes each with 6.5 ml. of DMF per gram resin.
2. To couple the amino acid, treat with the protected amino acid and N,N'-dicyclohexylcarbodiimide (50% on molar basis relative to the amino acid) in 80 ml. of 1:1 DMF:CH$_2$Cl$_2$ for 110 minutes.
3. Wash three times for three minutes each with 6.5 ml. of DMF per gram resin.
4. Wash three times for three minutes each with 6.5 ml. of CH$_2$Cl$_2$ per gram resin.
5. Wash three times for three minutes each with 6.5 ml. per gram resin of a mixture of 90% t-BuOH and 10% t-AmOH.
6. Wash three times for three minutes each with 6.5 ml. of CH$_2$Cl$_2$ per gram resin.
7. For neutralization, treat three times for three minutes each with 6.5 ml. per gram resin of a mixture of 4% diisopropylethylamine in CH$_2$Cl$_2$.
8. Wash three times for three minutes each with 6.5 ml. of CH$_2$Cl$_2$ per gram resin.
9. Wash three times for three minutes each with 6.5 ml. per gram resin of a mixture of 90% t-BuOH and 10% t-AmOH.
10. Wash three times for three minutes each with 6.5 ml. of CH$_2$Cl$_2$ per gram resin.

SCHEDULE C

Schedule C is the same as Schedule A in all respects except as to the amino acid coupling Step 10. Step 10 of Schedule A is replaced by a sequence of three steps as follows:
 (a) Wash three times for three minutes each with 6.5 ml. of DMF per gram resin.
 (b) To couple the amino acid, treat with the protected amino acid, active ester, in 80 ml. of a 3:5 mixture of DMF and CH$_2$Cl$_2$ for 10 hours.
 (c) Wash three times for three minutes each with 6.5 ml. of DMF per gram resin.

SCHEDULE D

Schedule D is the same as Schedule B in all respects except as to the amino acid coupling Step 2. Step 2 of Schedule D is as follows:
 To couple the amino acid, treat with the protected amino acid, active ester, in 80 ml. of a 5:3 mixture of DMF and CH$_2$Cl$_2$ for 10 hours.

C. L-Threonyl-L-isoleucyl-L-seryl-L-lysyl-L-alanyl-L-lysyl-glycyl-L-glutaminyl-L-prolyl-L-arginyl-L-glutamyl-L-prolyl-L-glutaminyl-L-valyl-L-tyrosyl-L-threonyl-L-leucyl-L-prolyl-L-prolyl-L-seryl-L-arginyl-L-glutamyl-L-glutamic acid To 16.5 g. of the resin product of Part B were added 23 ml. of anisole and 23 ml. of ethyl mercaptan. The mixture was frozen in a liquid $N_2$ bath, and 250 ml. of liquid HF were transferred into the mixture by distillation. The liquid $N_2$ bath was replaced by an ice water bath, and the mixture was stirred for 2 hours at 0° C. The HF then was removed in vacuo, and ethyl ether was added to the remainder to precipitate the peptide product. The precipitate was filtered, washed with ether, and air dried. The precipitate, comprising deblocked peptide and resin, was slurried in 25 ml. of 50% acetic acid and filtered. The residue (resin) then was rinsed with 10 ml. of 50% acetic acid after which it was reslurried in 0.2 M acetic acid, filtered and rinsed with 10 ml. of 50% acetic acid. The resin then was extracted four times with 30 ml. portions of 0.2 M acetic acid and washed with water. The washings and extracts were combined and filtered through glass fiber to provide a total of 350 ml. of 6.9% aqueous acetic acid containing the deblocked peptide product.

The acetic acid solution containing deblocked peptide product was applied to a 10×225 cm. Sephadex G-25F column which had been equilibrated with degassed 0.2 M acetic acid. The column was eluted with 0.2 M acetic acid by gravity flow for 16 hours and at 11 p.s.i. for the remainder. The optical density (OD) of the eluant was monitored with an Isco Model UA-5 using a 1.0 cm. flow cell and a filter for monitoring 280 nm. The following pools, described in terms of their elution and total volumes, were prepared:

| Pool No. | Elution Volume, ml. | Pool Volume, ml. |
|---|---|---|
| I | 0-9400 | 9400 |
| II | 9400-10420 | 1020 |
| III | 10420-10970 | 550 |
| IV | 10970-11435 | 465 |
| V | 11435-12165 | 730 |

Pool II, containing about 500 mg., was subjected to preparative reverse phase high performance liquid chromatography (HPLC) under the following conditions:

Column: 5.0 cm.×60 cm.
Packing: $C_{18}$ LP-1, capped
Solvent: 15% $CH_3CH$, 0.05 M $HCOONH_4$, to pH 4.25 with HCOOH
Flow Rate: about 10 ml./min.
Monitored at 280 nm A peak appeared at 1985 ml. to 2379 ml. elution volume. It was collected, lyophilized, and estimated by UV absorption to contain about 180 mg. of peptide.

The recovered peptide, dissolved in 50 ml. of 0.01 N HCl containing 7 M urea, was subjected to Sephadex G-50F chromatography under the following conditions:

Column: 5.0 cm.×215 cm.
Packing: Sephadex G-50 Fine
Solvent: 1 M acetic acid
Flow Rate: about 2.5 ml./min.

The product was collected at 2690 ml. to 3120 ml. elution volume, lyophilized, and estimated by UV absorption to contain about 80 mg. of peptide.

Amino acid analysis: Thr, 1.93; Ser, 2.03; Glu, 5.28; Pro, 4.19; Gly, 0.99; Ala, 1.00; Val, 0.99; Ile, 0.93; Leu, 1.02; Tyr, 0.98; Lys, 2.00; Arg, 2.04.

The above results represent the average of 21 hour and 72 hour hydrolysates ratioed to 0.25 of (Gly & Ala & Lys), with the exception that Thr and Ser were extrapolated to zero hours hydrolysis and Val was extrapolated to infinite hydrolysis time.

Biological Activity

The ability of compounds of this invention to modulate an immune response is demonstrated using a range of assays. In each of the following assays, the compound prepared by Example 2 is used.

A. Polyclonal Antibody Response Assay

This assay measures the activity of test compound in potentiating an in vitro polyclonal response using mouse spleen and human peripheral blood cells.

1. Mouse—For the generation of the polyclonal plaque-forming cell (PFC) response, mouse spleen cells were suspended to a concentration of $6 \times 10^6$/ml. in RPMI 1640 (Flow Laboratories, Rockville, Md.) supplemented with 2 mM L-glutamine, 1% BME vitamins (Grand Island Biological Co., N.Y.), 100 units penicillin, 100 µg. streptomycin, $5 \times 10^{-5}$ M 2-mercaptoethanol (2-ME), 0.5% fresh normal mouse serum, and 7.5% fetal calf serum (FCS). A predetermined quantity of test compound was added. Duplicate cultures of $6 \times 10^5$ cells/0.3 ml. were incubated in microtiter plates at 37° C. in 5% $CO_2$. The duplicate cultures were harvested on day 3 and assayed for a response to 2,4,6-trinitrophenyl (TNP) by the slide modification of the plaque assay described in N. K. Jerne and A. A. Nordin, Science 140, 405 (1963). Heavily conjugated TNP-sheep red blood cells (TNP-SRBC) were prepared according to the method described by J. Kettman and R. W. Dutton, J. Immunol. 104, 1558 (1970) and were used as the indicator red blood cell (RBC). Guinea pig serum was the source of complement (C) to develop the direct or IgM plaques. Results of the plaque-forming assay are shown in the following Table I and are expressed as mean PFC/$10^6$ original cells of duplicate pools±standard error.

TABLE I

| Polyclonal Antibody Production by Mouse Spleen Cells | |
|---|---|
| Compound, (µg/ml) | Direct Anti-TNP PFC/$10^6$ ± SE |
| — | 6 ± 7 |
| .025 | 87 ± 3 |
| 0.25 | 201 ± 5 |
| 2.5 | 31 ± 16 |

2. Human—This assay was carried out using human peripheral blood lymphocytes (PBL). PBL was prepared by diluting heparinized peripheral blood with two volumes of phosphate-buffered saline (PBS), 0.001 M phosphate pH 7.2, 0.15 M NaCl. Lymphocytes were separated by Ficoll-Paque (Pharmacia) gradient centrifugation as described in E. L. Morgan and W. O. Weigle, J. Exp. Med. 154, 778 (1981).

PBL suspensions were enriched for B and T cells by the neuraminidase-treated SRBC rosette technique described in Morgan and Weigle, supra. The non-rosetting cells were defined as B cell and monocyte enriched and the rosetting cells as T cell-enriched. The T cell populations were subjected to 2000 R of irradiation prior to use in the assay.

The human polyclonal antibody response was measured using a mixture of $1 \times 10^5$ B cells and $2 \times 10^5$ irradiated T cells to which were added a predetermined quantity of test compound. The cells were suspended and treated as in the above-described mouse polyclonal assay, with the exception that the cultures were harvested on day 6 instead of day 3. The results are provided in the following Table II.

TABLE II

| Polyclonal Antibody Production by Human Peripheral Blood Lymphocytes | |
|---|---|
| Compound (µg/ml) | Ig-Secreting Cells/$10^6$ B Cells ± SE |
| — | 65 ± 1 |
| .003 | 1,217 ± 37 |

B. In Vitro Anti-SRBC Adjuvant Assay

1. Mouse—Spleens were removed from mice which four to six weeks previously had been injected i.p. with 0.1 ml. of a 10% suspension of SRBC. A modified Mishell-Dutton culture system was employed for generation of antibody-producing cells. Cells were suspended to a concentration of $6 \times 10^6$/ml. of RPMI-1640 supplemented with 2 mM L-glutamine, 1% BME vitamins, 100 U penicillin, 100 µg. streptomycin, $5 \times 10^{-5}$ M 2-ME, 7.5% FCS, and 0.5% fresh normal mouse serum. The spleen cells at a concentration of $6 \times 10^5$ along with $5 \times 10^4$ SRBC and a predetermined amount of test compound were cultured in 0.3 ml. final volume in flatbottom microtiter plates for 4 days at 37° C. in 5% $CO_2$. The direct anti-SRBC response was measured by the slide modification of the Jerne and Nordin plaque assay. The results, shown in the following Table III, are recorded as direct anti-SRBC PFC/$10^6$ original cells±standard error.

TABLE III

| Enhancement of the Mouse in Vitro Anti-SRBC Response | | |
|---|---|---|
| Compound (µg/ml) | SRBC$^a$ | Direct Anti-SRBC PFC/$10^6$ ± SE |
| — | + | 129 ± 9 |
| 0.03 | + | 560 ± 18 |

$^a 5 \times 10^4$ SRBC/culture

2. Human—The primary anti-SRBC response was carried out as described by J. Misiti and T. A. Waldmann, J. Exp. Med. 154, 1069 (1981). Peripheral blood lymphocytes ($5 \times 10^6$) were cultured in 1 ml. of RPMI 1640 supplemented with 2 mM L-glutamine, 1% BME vitamins, 100 U penicillin, 100 µg. streptomycin, $5 \times 10^{-5}$ M 2-ME, and 10% SRBC-absorbed autologous human plasma. The desired amount of test compound plus $1 \times 10^5$ SRBC were added prior to culturing. The cultures were maintained in gas boxes which were rocked at 7 or 3.5 cycles/minute for 11 days. Every other day the cultures were fed a cocktail mixture containing autologous plasma as described by R. I. Mishell and R. W. Dutton, J. Exp. Med. 126, 423 (1967). The direct or IgM response was measured by the Jerne and Nordin plaque assay on day 11 of culture. The results, shown in Table IV following, are recorded as direct anti-SRBC PFC/culture±standard error.

TABLE IV

| Enhancement of the Human in Vitro Anti-SrBC Response | | |
|---|---|---|
| Compound (µg/ml) | SRBC$^a$ | Direct Anti-SRBC PFC/Culture ± SE |
| — | + | 49 ± 4 |
| 0.03 | + | 292 ± 16 |

$^a 1 \times 10^5$ SRBC/culture.

C. In Vivo Anti-SRBC Adjuvant Assay

Mice, in groups of 4, were given 0.1 ml. of a SRBC suspension intraperitoneally followed immediately by intravenous injection of saline or saline containing test compound. The spleens were assessed for PFC to SRBC five days after immunization. The results are shown in Table V following.

TABLE V

| Enhancement of the Primary in Vivo Anti-SRBC Response | | |
|---|---|---|
| SRBC$^a$ | Compound (µg/mouse) | Direct Anti-SRBC PFC/$10^6$ ± SE |
| + | — | 23 ± 3 |
| + | 10 | 120 ± 5 |

$^a$0.1 ml. of 0.1% suspension was injected/mouse.

D. Cell Mediated Lympholysis (CML) Assay

This assay measures the ability of test compound to augment the T cell cytolytic response.

1. Induction of Cytotoxic (Effector) Cells.

Normal C57BL/6 T cells ($2.5 \times 10^6$) are cultured for 5 days with $2.5 \times 10^5$ irradiated (2000R) CBA/CaJ spleen cells at 37° C. in 5% $CO_2$ (final volume-0.3 ml.) in flat bottom microtiter plates. The culture medium consisted of RPMI-1640 supplemented with 2 mM L-glutamine, 1% BME vitamins, 100 units penicillin, 100 mg. streptomycin, $5 \times 10^{-5}$ M 2-mercaptoethanol (2-ME), and 10% fetal calf serum (FCS).

2. Preparation of Target Cells.

Two days prior to assay, CBA/CaJ blast cells (target cells) are prepared in incubating $5 \times 10^5$ CBA/CaJ spleen cells per well with 20 µg./ml. lipopolysaccharide (LPS) in a manner as described above for normal T cells.

On the day of assay, blast cells are harvested and labeled with $^{51}Cr$ by incubating $2 \times 10^6$ blasts with 200 µCi $^{51}Cr$ (sodium chromate) for 60 minutes. The cells then are washed and resuspended in RPMI-1640 containing 10% FCS.

3. Assay

Varying numbers of effector cells are cultured with a constant number of labeled target cells for 4 hours in round bottom 12 mm. $\times$ 75 mm. plastic tubes. At the end of 4 hours, the cells are centrifuged at 1000 rpm for 5 minutes, and the resulting supernatant is analyzed for released $^{51}Cr$. The data, recorded as % Specific Release (SR), are determined as follows:

$$\% SR = \frac{\text{Experimental Release} - \text{Spontaneous Release}}{\text{Maximal Release} - \text{Spontaneous Release}} \times 100$$

in which Spontaneous Release is the amount of $^{51}Cr$ released in the absence of effector cells, and Maximal Release is the amount of $^{51}Cr$ released after freezing and thawing target cells three times.

The results are shown in Table VI following.

TABLE VI

| Compound (μg./ml.) | Ratio, Effector: Target Cells | % $^{51}$Cr Release |
|---|---|---|
| — | 10 | 12 ± 2 |
| 0.17 | 10 | 72 ± 2 |

E. Enhancement of the Peripheral Blood Lymphocytes (PBL) Proliferative Response to Tetanus Toxoid Antigen PBL (4×10⁵ cells) are cultured with 1 μg./ml. tetanus toxoid in RPMI-1640 supplemented with 2 mM L-glutamine, 1% BME vitamins, (00 units penicillin, 100 mg. streptomycin, and 10% human AB serum. The cultures were pulsed with 1 μCi [³H]thymidine (TdR) on day 6, harvested 24 hours later and counted using a Beta counter. The results are shown in Table VII following.

TABLE VII

Enhancement of PBL-Induced Proliferative Response to Tetanus Toxoid

| Compound (μg./ml.) | Tetanus Toxoid (μg./ml.) | [3H]TdR Uptake, cpm + SE |
|---|---|---|
| — | — | 5,133 ± 2,069 |
| — | 1 | 41,770 ± 372 |
| 0.013 | 1 | 101,730 ± 320 |

We claim:

1. Compound having the formula H-Thr-Ile-Ser-Lys-Ala-Lys-Gly-Gln-Pro-Arg-Glu-Pro-Gln-Val-Tyr-Thr-Leu-Pro-Pro-Ser-Arg-Glu-Glu-Hse in which Hse is homoserine or homoserine lactone.

2. A compound of the formula R-Thr-a-b-Lys-d-e-f-g-h-j-k-l-m-n-p-q-t-u-Pro-v-w-x-y-(z)$_r$-R$_1$ in which each amino acid residue has an L-configuration; R is hydrogen or $C_1$-$C_3$ alkyl; R$_1$ is OH or NR$_3$R$_4$ in which R$_3$ and R$_4$ independently are hydrogen or $C_1$-$C_3$ alkyl;
   a is Ile or Leu;
   b is Ser or Ala;
   d is Ala, Thr, Pro, Val, or Ser;
   e is Lys, Arg, Thr, or Gly;
   f is Gly, Val, or Asn;
   g is Gln, Lys, Ser, Glu, Pro, Ala, Asn, or Thr;
   h is Pro, Val, Thr, or Phe;
   j is Arg, Leu, Pro, or Phe;
   k is Glu, Ala, Ile, Met, or Pro;
   l is Pro, Lys, or Gln;
   m is Gln, Glu, or Val;
   n is Val or His;
   p is Tyr, His, or Leu;
   q is Thr, Val, or Leu;
   t is Leu, Ile, Met, or Pro;
   u is Pro or Gly;
   v is Ser or Pro;
   w is Arg, Gln, Glu, or Ser;
   x is Glu, Asp, Gln, or Asn;
   y is Glu, Gln, Gly, or Leu;
   z is Hse; and
   r is 0 or 1.

3. Compound of claim 2, in which
   a is Ile;
   b is Ser;
   d is Ala, Thr, Pro, or Ser;
   e is Lys or Arg;
   f is Gly;
   g is Gln, Lys, Ser, or Pro;
   h is Pro or Val;
   j is Arg or Leu;
   k is Glu, Ala, Ile, or Met;
   l is Pro;
   m is Gln or Glu;
   n is Val;
   p is Tyr;
   t is Leu, Ile, or Met;
   w is Arg;
   x is Glu or Asp; and
   y is Glu or Gln.

4. Compound of claim 3, in which
   d is Ala, Thr, or Ser;
   g is Gln;
   h is Pro;
   j is Arg;
   k is Glu;
   m is Gln;
   q is Thr; and
   t is Leu.

5. Compound of claim 2, in which
   a is Ile;
   b is Ser;
   d is Ala or Thr;
   e is Lys;
   f is Gly;
   g is Gln;
   h is Pro;
   j is Arg;
   k is Glu;
   l is Pro;
   m is Glu or Gln;
   n is Val;
   p is Tyr;
   q is Thr;
   t is Leu;
   u is Pro;
   v is Ser;
   w is Arg or Gln;
   x is Glu, Asp, or Gln; and
   y is Glu or Gly.

6. Compound of claim 5, in which r is 0.

7. Compound of claim 6, which compound has the formula R-Thr-Ile-Ser-Lys-Ala-Lys-Gly-Gln-Pro-Arg-Glu-Pro-Gln-Val-Tyr-Thr-Leu-Pro-Pro-Ser-Arg-Glu-Glu-R$_1$.

8. Compound of claim 7, in which R is hydrogen.

9. Compound of claim 8, in which R$_1$ is OH.

10. Compound of claim 6, which compound has the formula R-Thr-Ile-Ser-Lys-Ala-Lys-Gly-Gln-Pro-Arg-Glu-Pro-Gln-Val-Tyr-Thr-Leu-Pro-Pro-Ser-Arg-Asp-Glu-R$_1$.

11. Compound of claim 6, which compound has the formula R-Thr-Ile-Ser-Lys-Thr-Lys-Gly-Gln-Pro-Arg-Glu-Pro-Gln-Val-Tyr-Thr-Leu-Pro-Pro-Ser-Arg-Glu-Glu-R$_1$.

12. Compound of claim 6, which compound has the formula R-Thr-Ile-Ser-Lys-Thr-Lys-Gly-Gln-Pro-Arg-Glu-Pro-Glu-Val-Tyr-Thr-Leu-Pro-Pro-Ser-Arg-Glu-Glu-R$_1$.

13. Compound of claim 6, which compound has the formula R-Thr-Ile-Ser-Lys-Ala-Lys-Gly-Gln-Pro-Arg-Glu-Pro-Gln-Val-Tyr-Thr-Leu-Pro-Pro-Ser-Gln-Glu-Glu-R$_1$.

14. Compound of claim 3, which compound has the formula R-Thr-Ile-Ser-Lys-Ala-Lys-Gly-Pro-Pro-Arg-Ile-Pro-m-Val-Tyr-Leu-Leu-Pro-Pro-Pro-Arg-x-y-R$_1$, in which m is Gln or Glu; x is Asp or Asn; and y is Glu or Gln.

15. Compound of claim 6, which compound has the formula R-Thr-Ile-Ser-Lys-Thr-Lys-Gly-Gln-Pro-Arg-Glu-Pro-Gln-Val-Tyr-Thr-Leu-Pro-Pro-Ser-Arg-x-Gly-$R_1$, in which x is Glu or Gln.

16. Compound of claim 2, which compound has the formula R-Thr-Ile-Ala-Lys-Val-Thr-Val-Asn-Thr-Phe-Pro-Pro-Gln-Val-His-Leu-Leu-Pro-Pro-Pro-Ser-Glu-Glu-$R_1$.

17. Compound of claim 2, which compound has the formula R-Thr-Leu-Ser-Lys-Ser-Gly-Asn-Thr-Phe-Arg-Pro-Gln-Val-His-Leu-Leu-Pro-Pro-Pro-Ser-w-x-Leu-$R_1$, in which w is Glu or Gln and x is Glu or Gln.

* * * * *